United States Patent
Woods et al.

(10) Patent No.: US 11,337,605 B2
(45) Date of Patent: May 24, 2022

(54) SIMULATOR FOR THE EVALUATION OF A CONCUSSION FROM SIGNS DISPLAYED DURING A VISUAL CRANIAL NERVE ASSESSMENT

(71) Applicant: KbPort LLC, Pittsburgh, PA (US)

(72) Inventors: Jerry Woods, Pittsburgh, PA (US); Clifford D. Olmstead, San Francisco, CA (US); Gregory P. Angell, Pittsburgh, PA (US)

(73) Assignee: KbPort, LLC, Pittsburgh, PA (US)

( * ) Notice: Subject to any disclaimer, the term of this patent is extended or adjusted under 35 U.S.C. 154(b) by 336 days.

(21) Appl. No.: 16/574,592

(22) Filed: Sep. 18, 2019

(65) Prior Publication Data

US 2020/0085297 A1    Mar. 19, 2020

Related U.S. Application Data

(60) Provisional application No. 62/733,280, filed on Sep. 19, 2018.

(51) Int. Cl.
*A61B 3/113* (2006.01)
*G06F 3/01* (2006.01)
*A61B 3/06* (2006.01)
*A61B 3/00* (2006.01)
*A61B 3/11* (2006.01)

(52) U.S. Cl.
CPC .............. *A61B 3/113* (2013.01); *A61B 3/06* (2013.01); *G06F 3/013* (2013.01); *A61B 3/0008* (2013.01); *A61B 3/11* (2013.01)

(58) Field of Classification Search
CPC ......... A61B 3/113; A61B 3/06; A61B 3/0008; A61B 3/11; G06F 3/013; G09B 23/28; G09B 23/30
USPC ......................................................... 351/209
See application file for complete search history.

(56) References Cited

U.S. PATENT DOCUMENTS

| 2012/0075168 A1* | 3/2012 | Osterhout | G06F 3/011 345/8 |
| 2014/0268356 A1* | 9/2014 | Bolas | G02B 27/017 359/630 |
| 2018/0008141 A1* | 1/2018 | Krueger | A61B 5/11 |

* cited by examiner

*Primary Examiner* — Mohammed A Hasan
(74) *Attorney, Agent, or Firm* — Buchanan Ingersoll & Rooney PC (57) ABSTRACT

Embodiments relate to a system for generating simulated eye movements and eye responses related to concussion symptoms for training medical practitioners. The system includes a computer device with a display that displays the pair of simulated eyes. Scenarios are generated and executed, in which simulated eye movements and responses to external stimuli are representative of typical symptoms associated with having a concussion. A user (e.g., medical trainee or medical trainer) provides external inputs e.g., voice commands, stylus movements, etc.) and assess eye movements provided by the scenarios and eye responses to the external inputs.

15 Claims, 6 Drawing Sheets

SIMULATOR FOR THE EVALUATION OF A CONCUSSION FROM SIGNS DISPLAYED DURING A VISUAL CRANIAL NERVE ASSESSMENT

CROSS-REFERENCE TO RELATED APPLICATIONS

This patent application is related to and claims the benefit of U.S. Provisional Patent Application No. 62/733,280, filed on Sep. 19, 2018, which is hereby incorporated by reference in its entirety.

FIELD OF THE INVENTION

Embodiments pertain to a system for generating simulated eye movements and eye responses related to concussion symptoms for training medical practitioners.

BACKGROUND OF THE INVENTION

Accurate diagnosis of a concussion is critical in neurological care. Concussions and post-concussive syndrome should be monitored closely to avoid negative outcomes, and an early accurate diagnosis can contribute to a positive patient trajectory if abnormal findings are identified. By simulating key aspects of the diagnostic criteria of a concussion, health care practitioners can be better trained to identify the signs of a concussion, thereby improving concussion diagnosis accuracy in a clinical setting. Conventional techniques for training medical practitioners fail to provide a system that generates realistic symptoms to facilitate robust and comprehensive medical assessment schemes.

SUMMARY OF THE INVENTION

The system generates a pair of simulated eyes configured to provide simulated eye movements associated with the physiological condition of a concussion so as to allow medical trainees to obtain training related to assessing patients. The system includes a computer device with a display that displays the pair of simulated eyes. Scenarios can be generated and executed, in which simulated eye movements and responses to external stimuli are representative of typical symptoms associated with having a concussion. A user (e.g., medical trainee or medical trainer) can provide external inputs (e.g., voice commands, stylus movements, etc.) and assess eye movements provided by the scenarios and eye responses to the external inputs (i.e., the external stimuli). The assessments are used to develop and improve upon the diagnosis skills of the medical trainee.

In at least one embodiment, a simulator for evaluating symptoms of a concussion includes a computer device in operative association with a display and a stylus. The computer device is configured to generate a pair of simulated eyes via the display. The pair of simulated eyes includes a first eye comprising a first pupil; and a second eye comprising a second pupil. The display has a front face, a plurality of latitudinal axes, and a plurality of longitudinal axes. The first pupil is located at a first intersecting point of a latitudinal axis and a longitudinal axis, and the second pupil is located at a second intersecting point of a latitudinal axis and a longitudinal axis. The display is configured to generate textual and/or audible responses to verbal questions or verbal commands. The stylus has a shaft and a tip. The tip includes a marker. The computer device has a sensor configured to detect proximity and motion of the marker. The computer device is configured to generate eye movements in accordance with at least one concussion scenario symptom and to generate eye responses to an external input, the external input including voice commands and movements of the stylus.

In at least one embodiment, the stylus has a light source, in at least one embodiment, the external input further includes light from the light source.

In at least one embodiment, the at least one concussion scenario symptom includes a plurality of concussion scenario symptoms. The plurality of concussion scenario symptoms includes a first scenario symptom comprising eye movements and eye responses associated with diplopia; a second scenario symptom comprising eye movements and eye responses associated with sensitivity to light and/or photophobia; a third scenario symptom comprising eye movements and eye responses associated with vision loss; a fourth scenario symptom comprising eye movements and eye responses associated with eye or ocular pain; a fifth scenario symptom comprising eye movements and eye responses associated with abnormal eye movements; a sixth scenario symptom comprising eye movements and eye responses associated with visual motion sensitivity; and a seventh scenario symptom comprising eye movements and eye responses associated with vertical heterophoria.

Some embodiments include generating the pair of simulated eyes in a normal state. The normal state includes the first pupil and the second pupil being located on a same latitudinal axis. The normal state also includes the first pupil and the second pupil are separated by a constant distance $D_{eye}$.

In some embodiments, the first scenario symptom includes $D_{eye}$ increasing or decreasing and/or the first pupil and/or the second pupil not being located on the same latitudinal, axis as the stylus tip is moved from position $D_2$ to position $D_1$, wherein $D_2$ and $D_1$ are distances from the front face of the display, $D_2$ being a greater distance than $D_1$.

In some embodiments, the stylus has a light source. The first eye has a first eyelid. The second eye has a second eyelid. The second scenario symptom includes at least one of: the first eyelid and/or the second eyelid blinks, squints, or closes as the light source with an intensity and/or an angle of incidence within predetermined ranges is shown at or near the first pupil and/or second pupil to mimic typical eyelid behavior; and the first pupil and/or the second pupil dilates as the light source with an intensity and/or an angle of incidence within predetermined ranges is shown at or near the first pupil and/or second pupil to mimic typical eyelid behavior.

In some embodiments, the stylus further has a light source. The first eye has first eyelid. The second eye has a second eyelid. The third scenario symptom includes at least one of: the first pupil and/or the second pupil does not track the stylus tip as the stylus tip is moved; the first eyelid and/or the second eyelid does not blink, squint, or close as the stylus tip is rapidly moved from position $D_2$ to position $D_1$, wherein $D_2$ and $D_1$ are distances from the front face of the display, $D_2$ being a greater distance than $D_1$; and the first pupil and/or the second pupil does not dilate as the light source with an intensity and/or an angle of incidence within predetermined ranges is shone at or near the first pupil and the second pupil to mimic typical pupil behavior.

In some embodiments, the first pupil and/or the second pupil does not track the stylus tip as the stylus tip is moved within a blind spot; the first eyelid and/or the second eyelid does not blink, squint, or close as the stylus tip is rapidly moved from position $D_2$ to position $D_1$, wherein $D_2$ and $D_1$ are within the blind spot; the first pupil and/or the second pupil does not dilate as the light source with an intensity and/or an angle of incidence within predetermined ranges is shone at or near the first pupil and the second pupil to mimic typical pupil behavior, the light source being within the blind spot. The blind spot is defined as a predetermined volume of space in front of the front face.

In some embodiments, the first eye has a first sclera. The second eye has a second sclera. The fourth scenario symptom includes at least one of: textual and/or audible responses to verbal questions about pain, the textual and/or audible response being a confirmation that there is pain; and the first sclera and/or the second sclera having a red or pink color.

In some embodiments, the fifth scenario symptom includes at least one of: the first pupil and/or the second pupil exhibiting a slowed or delayed tracking of the stylus tip as the stylus tip is moved; and the first pupil and/or the second pupil deviating focus from the stylus tip, focus on the stylus tip being defined as the first pupil and/or the second pupil aiming at a point in space where the stylus tip is located.

In some embodiments, the sixth scenario symptom includes motioning the stylus and textual and/or audible responses to verbal questions about disorientation, discomfort, and/or dizziness, the textual and/or audible response being a confirmation that there is disorientation, discomfort, and/or dizziness.

In some embodiments, the seventh scenario symptom includes first pupil and the second pupil not being located on the same latitudinal axis; and textual and/or audible responses to verbal questions about pain and/or discomfort, the textual and/or audible response being a confirmation that there is pain and/or discomfort.

In some embodiments, a concussion tutorial is generated for the at least one concussion scenario symptom.

In at least one embodiment, a manikin simulator for evaluating symptoms of a concussion includes a medical simulator device configured to resemble at least a portion of a human anatomy, the medical simulator device having an eye simulator portion The eye simulator portion includes a computer device in operative association with a display and a stylus. The computer device is configured to generate a pair of simulated eyes via the display. The pair of simulated eyes has a first eye comprising a first pupil; and a second eye comprising a second pupil. The display has a front face, a plurality of latitudinal axes, and a plurality of longitudinal axes. The first pupil is located at a first intersecting point of a latitudinal axis and a longitudinal axis, and the second pupil is located at a second intersecting point of a latitudinal axis and a longitudinal axis. The display is configured to generate textual and/or audible responses to verbal questions or verbal commands. The stylus has a shaft and a tip. The tip includes a marker. The computer device has a sensor configured to detect proximity and motion of the marker. The computer device is configured to generate eye movements in accordance with at least one concussion scenario symptom and to generate eye responses to an external input, the external input being voice commands and movements of the stylus.

In some embodiments, the at least one concussion scenario symptom includes a plurality of concussion scenario symptoms. In some embodiments, the plurality of concussion scenario symptoms includes: a first scenario symptom comprising eye movements and eye responses associated with diplopia; a second scenario symptom comprising eye movements and eye responses associated with sensitivity to light and/or photophobia; a third scenario symptom comprising eye movements and eye responses associated with vision loss; a fourth scenario symptom comprising eye movements and eye responses associated with eye or ocular pain; a fifth scenario symptom comprising eye movements and eye responses associated with abnormal eye movements; a sixth scenario symptom comprising eye movements and eye responses associated with visual motion sensitivity; and a seventh scenario symptom comprising eye movements and eye responses associated with vertical heterophoria.

In at least one embodiment, a simulator system for evaluating symptoms of a concussion includes a first computer device in operative association with a display and a stylus. The first computer device is configured to generate a pair of simulated eyes via the display. The pair of simulated eyes includes a first eye comprising a first pupil; and a second eye comprising a second pupil. The display has a front face, a plurality of latitudinal axes, and a plurality of longitudinal axes. The first pupil is located at a first intersecting point of a latitudinal axis and a longitudinal axis, and the second pupil is located at a second intersecting point of a latitudinal axis and a longitudinal axis. The display is configured to generate textual and/or audible responses to verbal questions or verbal commands. The stylus has a shaft and a tip. The tip includes a marker. The first computer device has a sensor configured to detect proximity and motion of the marker. The first computer device is configured to generate eye movements in accordance with at least one concussion scenario symptom and to generate eye responses to an external input, the external input comprising voice commands and movements of the stylus. The system also includes a second computer device in communication with the first computer device via a communications network. The second computer device is configured to select the at least one concussion scenario symptom to be executed by the first computer device.

In some embodiments, the first computer device is pan of a manikin simulator.

In some embodiments, the at least one concussion scenario symptom includes a plurality of concussion scenario symptoms. The plurality of concussion scenario symptoms includes: a first scenario symptom comprising eye movements and eye responses associated with diplopia; a second scenario symptom comprising eye movements and eye responses associated with sensitivity to light and/or photophobia; a third scenario symptom comprising eye movements and eye responses associated with vision loss; a fourth scenario symptom comprising eye movements and eye responses associated with eye or ocular pain; a fifth scenario symptom r comprising eye movements and eye responses associated with abnormal eye movements; a sixth scenario symptom comprising eye movements and eye responses associated with visual motion sensitivity; and a seventh scenario symptom comprising eye movements and eye responses associated with vertical heterophoria.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present innovation will be more apparent from the following more particular description thereof, presented in conjunction with the following drawings. Like reference numbers used in the drawings may identify like components.

DETAILED DESCRIPTION OF THE INVENTION

The following description is of exemplary embodiments that are presently contemplated for carrying out the present invention. This description is not to be taken in a limiting sense, but is made merely for the purpose of describing the general principles and features of the present invention. The scope of the present invention is not limited by this description.

Figure 1:
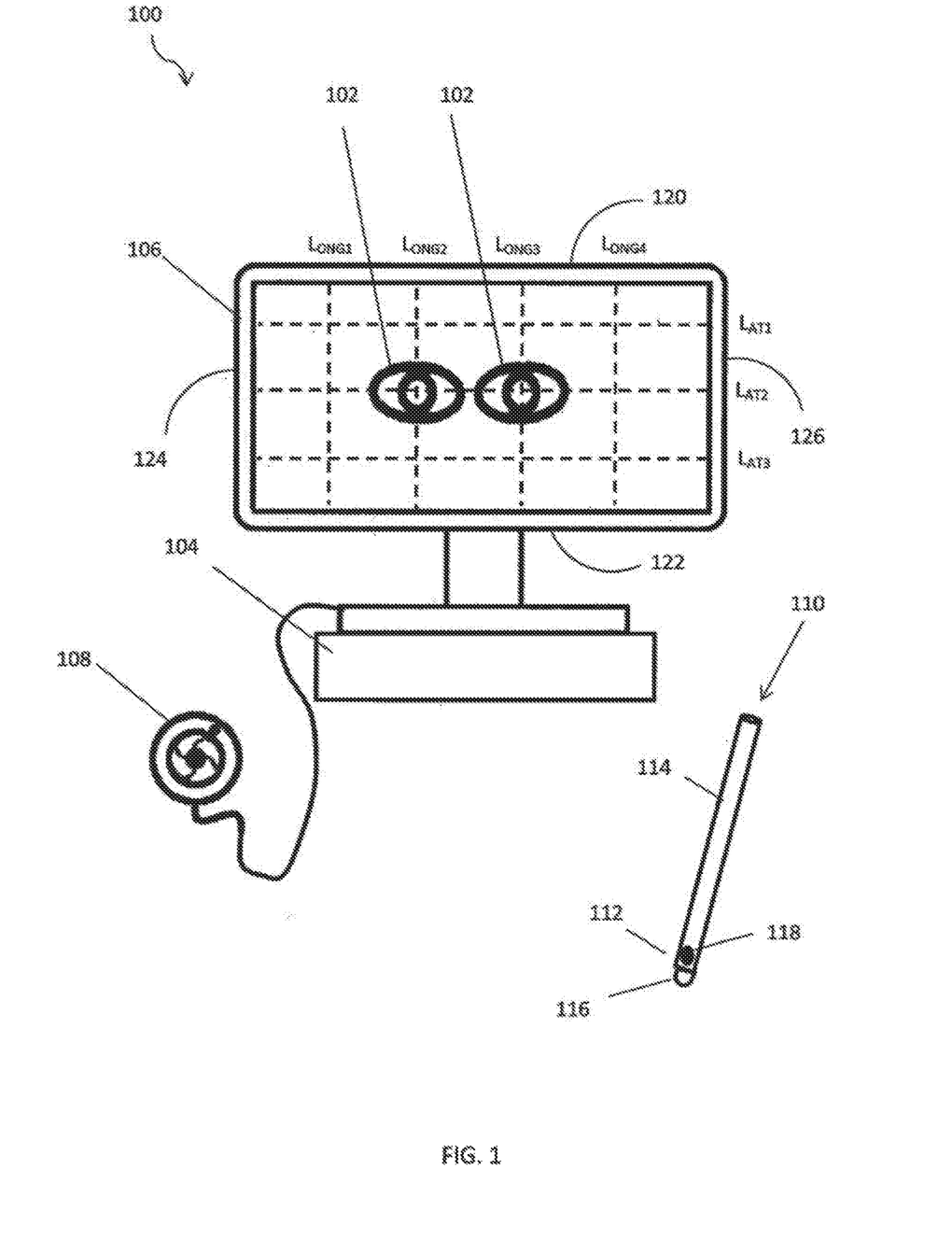
FIG. 1 shows an embodiment of the eye simulator system with a display as a peripheral device to a computer device.
Figure 2:
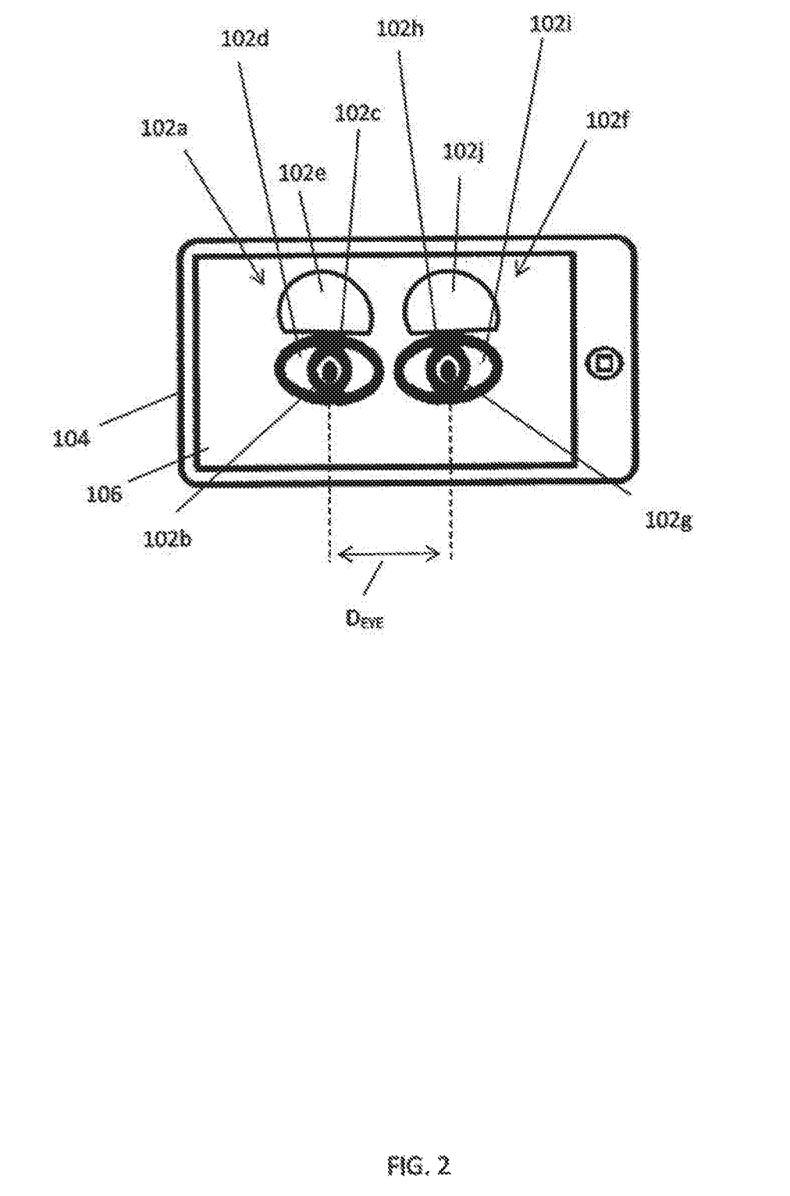
FIG. 2 shows an embodiment of the eye simulator system with a display as an integral component to a computer device.

Referring to FIGS. 1-2, embodiments relate to a system 100 configured to provide simulated responses via eye movements associated with a physiological condition. For example, the system 100 generates a simulated eye 102 configured to provide simulated eye movements associated with the physiological condition so as to allow medical trainees to obtain training related to assessing patients. The training can be used to improve a medical trainee's ability to accurately diagnose physiological conditions by structuring the assessments to require medical trainees to perform evaluations of the simulated eye's 102 visual field, pupillary response, extraocular movements, etc. In some embodiments, the system 100 is configured to provide training regarding physiological conditions associated with a concussion. For example, the simulated eye movements can be sluggish, be a reduced or asymmetric response to stimuli, be a restricted range of motion, a sluggish or asymmetric pupillary response, and/or other movements associated with a concussion. The system 100 is used to develop the medical trainee's skills in identifying any one or combination of these eye movements and associate them with symptoms of a concussion.

The system 100 includes at least one computer device 104. Any of the computer devices 104 described herein has a processor operatively associated with a non-transitory, non-volatile memory. The computer device 104 has a display 106 configured to display at least one simulated eye 102, which can include a pair of simulated eyes 102. The display 106 can be a liquid crystal display, a light emitting diode display, a plasma display panel, etc. Embodiments disclosed herein may describe use of a pair of simulated eyes 102, but it is understood that any number of simulated eyes 102 can be displayed. In some embodiments, the display 106 is a separate peripheral device to the computer device 104. For example, the computer device 104 can be a desktop-style computer with a display monitor as the display 106 (see FIG. 1). In some embodiments, the display 106 is integral to the computer device 104. For example, the computer device can be a laptop, tablet, smartphone, etc. with a display screen as the display 106 (see FIG. 2).

In some embodiments, the computer device 104 has a sensor 108 that is configured to detect external inputs. The sensor 108 can be any one or combination of a proximity sensor, motion sensor, temperature sensor, electromagnetic coil, light sensor, a charged coupled device, a photodiode, a camera, a microphone, etc. The sensor 108 is in operative association with the processor of the computer device 104. The sensor 108 can be integral to the computer device 104 (see FIG. 2) or be a separate peripheral device connected to the computer device 104 (see FIG. 1). The external inputs are inputs from a user (e.g., medical trainee or medical trainer), such as voice commands, movements of a stylus, movements of a light pointer or flashlight, movements of a finger, etc. In at least one embodiment, the system 100 includes a stylus 110. The stylus 110 has a shaft 114 and a tip 112. The tip 112 can include a marker 118 (e.g., a radio frequency identification tag, an electromagnetic coil, a material exhibiting a certain conductance, a material exhibiting a certain reflectance, etc.) that is detectable by the sensor 108 of the computer device 104. In some embodiments, the tip 112 includes a light source 116 (e.g., a light emitting diode) with an operable on/off switch and an intensity of luminance control switch. This can be done to so that a user can use the stylus 110 as a light pointer or a flashlight.

Application software is stored in the memory of the computer device 104 and is configured to cause the processor of the computer device 104 to display a pair of simulated eyes 102 via the display 106. Each simulated eye 102 is a virtual eye that is configured to resemble a human eye (e.g., each simulated eye can have a lens, cornea, pupil, iris, etc.). The pair of simulated eyes 102 includes a first eye 102a and a second eye 102f. The first eye 102a has a first pupil 102b, a first iris 102c, a first sclera 102d, and a first eye lid 102e. The second eye 102f has a second pupil 102g, a second iris 102h, a second sclera 102i, and a second eye lid. 102j. The display of these features can be black-and-white, grayscale, or in color. For example, the eye lid 102e, 102j can be skin colored, the sclera 102d, 102i can be white, the iris 102c, 102h can be brown, hazel, blue, etc., and the pupil 102b, 102g can be black.

The application software also controls the simulated movement of the pair of simulated eyes 102. For example, the application software is programmed to execute at least one symptom scenario. Any one or combination of symptom scenarios can be related to a physiological condition. The physiological condition can be a concussion (e.g., abnormal eye movement, positioning, and/or responses), conjunctivitis (e.g., redness to the sclera 102d, 102i, etc.), hepatitis (e.g., yellowing to the sclera 102d, 102i), glaucoma (e.g., clouding of the sclera 102d, 102i), pupil dilation, pupil miosis, pupil misalignment (e.g., strabismus, amblyopia, etc.), etc.

The system 100, unless executing a symptom scenario, displays a normal state for the simulated eyes 102a, 102f. The normal state can be defined as placement, aiming, movement, and response of the pupils 102b, 102g when the person is not experiencing a physiological condition. The normal state includes the system 100 displaying the pair of simulated eyes 102a, 102f on the display 106 juxtaposed to each other, as would be with a normal anatomical position in a human, and without any abnormal coloring of the sclera 102d, 102i. The normal state also includes the pupil 102b, 102g of each simulated eye 102a, 102f o aiming at a same point in space. For example, it is contemplated for the display 106 to be a planar object having a top side 120, a bottom side 122, a left side 124, a right side 126, and a front face 128 (the left and right sides are from the point of view of a user looking at the display 106). In the normal state, the first eye 102a and the second eye 102f are displayed on a same latitudinal axis (e.g., $L_{AT1}$, $L_{AT2}$, $L_{AT3}$, etc.) with the first eye 102a being more proximate to the left side 124 than the second eye 102f, and the second eye 102f being more proximate the right side 126 than the first eye 102a. Being on the same latitudinal axis means that if the first eye 102a is located on $L_{AT1}$ then the second eye 102f is also located on $L_{AT1}$. If the first eye 102a is located on $L_{AT2}$ then the second eye 102f is also located on $L_{AT2}$. As a non-limiting example and as shone in FIG. 1, the first eye 102a is located at ($L_{ONG2}$, $L_{AT2}$) and the second eye 102f is located at ($L_{ONG3}$, $L_{AT2}$). Under the normal state, the first pupil 102b and the second pupil 102g are separated by a distance $D_{eye}$, $D_{eye}$ being a distance along a latitudinal axis. Under the normal state, $D_{eye}$, remains constant, regardless of the induced movement or response from the user. In addition, under the normal state, the first pupil 102b and the second pupil 102g are always located on a same latitudinal axis. As noted above, being on the same latitudinal axis means that if the first pupil 102b is located on $L_{AT1}$ then the second pupil 102g is also located on $L_{AT1}$. As will be explained in detail later, the pupils 102b, 102g can move (e.g., can be caused to track the movement of a stylus 110). Under the normal state, the pupils 102b, 102g move in unison, and thus is the first pupil 102b moves from $L_{AT1}$ to $L_{AT2}$, the second pupil 102g moves in unison with the first pupil 102b from $L_{AT1}$ to $L^{AT2}$. In addition, under the normal state, the first pupil 102b and the second pupil 102g are always separated by a constant regardless of how the pupils 102b, 102g are caused to move.

As noted above, the first pupil 102b and the second pupil 102g are aiming at a same point in space under the normal state. The application software can be programmed to cause the pupils 102b, 102g to appear to be pointing to a single point in space, and a user can use the stylus 110 and/or voice commands to cause the pupils 102b, 102g to move and focus on a different point in space. For example, a user can issue a voice command to ask the computer device 104 to "look down", in which each of the first pupil 102b and the second pupil 102g move from $L_{AT2}$ to $L_{AT3}$ so as to appear to be looking down. Other directions can be used (e.g., "look up", "look left", etc.). A voice command by the user is detected by the microphone and analyzed using voice recognition techniques. As another example, a user can issue a voice command to ask the computer device 104 to "track the stylus", in which each of the first pupil 102b and the second pupil 102g moves to follow the stylus tip 112 as the user moves the stylus 110. This can be achieved by the computer device sensor 108 sensing the marker 118 in the tip 112 and computing a location of the tip 112 so as to cause the first pupil 102b and the second pupil 102g to move and appear to be looking at the tip 112 as the stylus 110 is moved. It should be noted that the display of the simulated eyes 102a, 102f can be 3-dimensional or include depth perception techniques so as to provide more realistic movement, tracking, and aiming of the pupils 102b, 102g. Under the normal state, the first pupil 102b and the second pupil 102g move in union to always appear to be aiming at a same point in space.

In some embodiments, the application software is programmed to execute symptom scenarios related to a concussion (i.e., the physiological condition being assessed by the medical trainee is a concussion). Each concussion scenario symptom provides certain eye movements and eye responses associated with a particular symptom or set of symptoms linked to having concussion. For example, a plurality of concussion scenario symptoms can be generated. This can include a first concussion scenario symptom, a second concussion scenario symptom, a third concussion scenario symptom, a fourth concussion scenario symptom, a fifth concussion scenario symptom, a sixth concussion scenario symptom, a seventh concussion scenario symptom, etc. Each scenario symptom is associated with eye movements and eye responses related to a concussion symptom. For example, typical concussion symptoms (as they relate to eye movements and eye responses) include diplopia, sensitivity to light and/or photophobia, vision loss, eye or ocular pain, abnormal eye movements, visual motion sensitivity, and vertical heterophoria. Each scenario symptom can be modeled to include any one or combination of eye movements and eye responses related to diplopia, sensitivity to light and/or photophobia, vision loss, eye or ocular pain, abnormal eye movements, visual motion sensitivity, and vertical heterophoria. While these are the most common, one skilled in the art will appreciate that other symptoms can be used.

During training, the computer device 104 operates a sequence of any one or combination of scenario symptoms and/or symptoms of a normal state, to allow a medical trainee to perform assessments. In addition, or in the alternative, a user (medical trainee or medical trainer) selects a scenario symptom (or portions of a scenario symptom) and/or symptoms of a normal state (or portions of symptoms of a normal state) to operate. Thus, the system 100 can generate a mix of simulated eye movements and simulated eye responses pertaining to a normal state and/or a scenario symptom to provide robust training programs for medical trainees. A medical trainee uses external inputs as part of his/her assessment and the computer device 104 causes the simulated eyes 102a, 102f to move and/or respond in accordance with the scenario symptom being operated.

Figure 3:
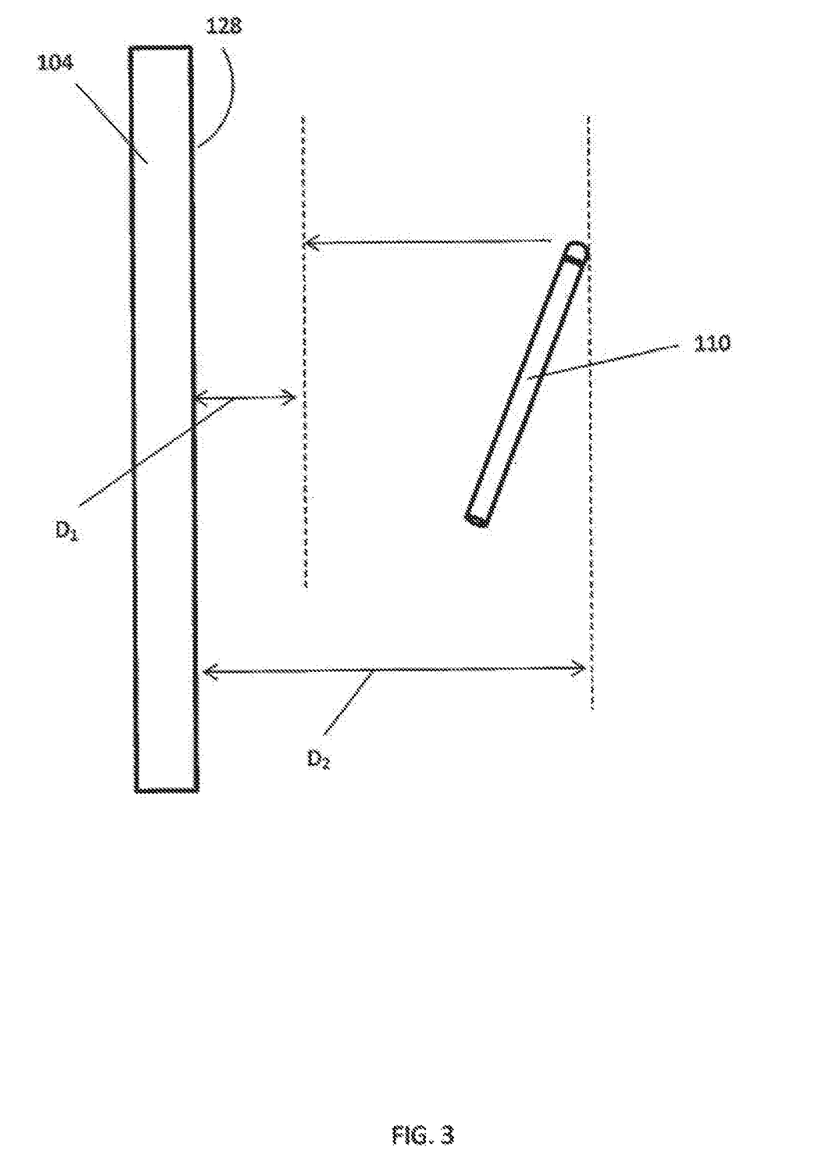
FIG. 3 shows an embodiment of the eye simulator system illustrating a stylus movement that can be used to assess a symptom related to a person having a concussion.

The first scenario symptom is eye movements and eye responses related to the concussion symptom of diplopia (e.g., blurred or double vision). Diplopia can result from damage to the muscle and/or nerves that lead to convergence insufficiency (e.g., the alignment of the eyes diverge when trying to focus on nearby objects). When executing the first scenario symptom, the system 100 generates simulated eye movements and simulated eye responses to allow a medical trainee to assess eye movement and eye responses related to diplopia. A medical trainee issues a voice command to ask the computer device 104 to "track the stylus". A medical trainee then uses a stylus 110 movement of advancing the stylus tip 112 from a position $D_2$ from the display 106 to a position $D_1$ from the display 106, wherein position D is a greater distance than distance $D_1$. (See FIG. 3). As the stylus tip 112 is moved, the computer device 104 detects the motion of the stylus tip 112. Under a normal state, each of the first pupil 102b and the second pupil 102g follows the stylus tip 112 so that each maintains aim on the stylus tip 112 (i.e., each of the first pupil 102b and the second pupil 102g maintain aim on a same point in space, which is the stylus tip 112). For example, as the stylus tip 112 is moved from $D_2$ to $D_1$. Each of the first pupil 102b and the second pupil 102g move so as to appear to be following the stylus tip 112, while the first pupil 102b and the second pupil 102g maintain the constant separation distance of $D_{eye}$ and are both located on a same latitudinal axis. Under the first scenario, the system 100 causes the first pupil 102b and/or the second pupil 102g to misalign as the stylus tip 112 is moved from position $D_2$ to position $D_1$. The misaligning is defined as deviating from the normal state by the first pupil 102b or the second pupil 102g not aiming at a same point in space (e.g., one of the first pupil 102b or the second pupil 102g not aiming at the stylus tip 112). For example, as the stylus tip 112 is moved from $D_2$ to $D_1$, $D_{eye}$ increases or decreases (e.g., does not remain constant) and/or the first pupil 102b is not on the same latitudinal axis as the second pupil 102g.

The second scenario symptom is eye movements and eye responses related to the concussion symptom of sensitivity to light and/or photophobia. When executing the second scenario symptom, the system 100 generates simulated eye movements and simulated eye responses to allow a medical trainee to assess eye movement and eye responses related to sensitivity to light and/or photophobia. A medical trainee issues a voice command to ask the computer device 104 to "keep the eye open". A medical trainee uses a light source 116 to shine it at or near the first pupil 102b and/or the second pupil 1022. The intensity and angle of incidence is such that a patient without sensitivity to light and/or photophobia would not blink, not squint, or not exhibit pupil dilation. Thus, under a normal state, each of the first eyelid 102e, 102j and the second eyelid 102e, 102j does not blink, squint, or close. In addition, under the normal state, each of the first pupil 102b and the second pupil 102g does not dilate. For example, as the light source 116 is shone at or near the first pupil 102b and/or second pupil 102g with an intensity and/or an angle of incidence within predetermined ranges, the first eyelid 102e, 102j and/or the second eyelid 102e, 102j does not blink, squint, or close and the first pupil 102b and/or the second pupil 102g does not dilate, to mimic typical eyelid/pupil behavior. Under the second scenario, as the light source 116 is shone at or near the first pupil 102b and/or second pupil 102g with an intensity and/or an angle of incidence within predetermined ranges, the system 100 causes: 1) the first eyelid 102e, 102j and/or the second eyelid 102e, 102j to blink, squint, or close; and/or 2) the first pupil 102b and/or the second pupil 102g to dilate, to mimic typical eyelid/pupil behavior.

The third scenario symptom is eye movements and eye responses related to the concussion symptom of vision loss. Vision loss can be complete, partial, limited to a certain eye, limited to a certain spot in the field of vision (e.g., a blind spot), etc. When executing the third scenario symptom, the system 100 generates simulated eye movements and simulated eye responses to allow a medical trainee to assess eye movement and eye responses related to vision loss. A medical trainee uses voice commands, stylus 110 movements, and/or shining of a light source 116 to induce: 1) tracking (e.g., causing the pupil to follow the stylus tip 112 as the pupils 102b, 102g would do under a normal state); 2) blinking, squinting, or closing of the eyelid 102e, 102j (e.g., rapid movement of the stylus tip 112 from $D_2$ to $D_1$ that would cause blinking, squinting, or closing of the eyelid 102e, 102j under a normal state); and/or 3) pupil dilation e.g, using an intensity and angle of incidence of light that would cause pupil dilation eyes in a normal state). Under a normal state, each of the first pupil 102b and the second pupil 102g: 1) tracks the stylus tip 112 as the stylus 110 is moved; 2) each of the first eyelid 102e, 102j and the second eyelid 102e, 102j blinks, squints, or closes the eyelid 102e, 102j as the stylus tip 112 is moved rapidly from $D_2$ to $D_1$; and/or 3) each of the first pupil 102b and the second pupil 102g dilates as the light source 116 with an intensity and/or an angle of incidence within predetermined ranges is shone at or near the first pupil 102b and the second pupil 102g, to mimic typical eyelid/pupil behavior. Under the third scenario, the system 100 causes: 1) the first pupil 102b and/or the second pupil 102g to not track the stylus tip 112 as the stylus 110 is moved; 2) the first eyelid 102e, 102j and/or the second eyelid 102e, 102j to not blink, squint, or close the eyelid 102e, 102j as the stylus tip 112 is moved rapidly from $D_2$ to $D_1$; and/or 3) the first pupil 102h and/or the second pupil 102g to not dilate as the light source with an intensity and/or an angle of incidence within predetermined ranges is shone at or near the first pupil 102b and the second pupil 102g, to mimic typical eyelid/pupil behavior.

As noted above, vision loss from a concussion can be limited to a certain spot in the field of vision so as to form a blind spot. Thus, in some embodiments of the third scenario is configured so that the first simulated eye 102 and the second simulated eye 102 exhibit behavior of the normal state unless the external input is within a predetermined blind spot. The blind spot can be a volume of space in front of the front face 128 of the display 106. For example, the blind spot can be the volume of space in front of the front face 128 of the display 106 that is confined by the sector defined by $L_{ONG3}$, $L_{ONG4}$, $L_{AT2}$, $L_{AT3}$. When the external input is outside of the blind spot, each of the first pupil 102b and the second pupil 102g: 1) tracks the stylus tip 112 as the stylus 110 is moved; 2) each of the first eyelid 102e, 102j and the second eyelid 102e, 102j blinks, squints, or closes the eyelid 102e, 102j as the stylus tip 112 is moved rapidly from $D_2$ to $D_1$ and/or 3) each of the first pupil 102b and the second pupil 102g dilates as the light source with an intensity and/or an angle of incidence within predetermined ranges is shone at or near the first pupil 102b and the second pupil 102g, to mimic typical eyelid/pupil behavior. When the external input is inside of the blind spot, the system 100 causes: 1) the first pupil 102b and/or the second pupil 102g to not track the stylus tip 112 as the stylus 110 is moved; 2) the first eyelid 102e, 102j and/or the second eyelid 102e, 102j to not blink, squint, or close the eyelid 102e, 102j as the stylus tip 112 is moved rapidly from $D_2$ to $D_1$; and/or 3) the first pupil 102b and/or the second pupil 102g to not dilate as the light source with as intensity and/or an angle of incidence within predetermined ranges is shone at or near the first pupil 102b and the second pupil 102g, to mimic typical eyelid/pupil behavior.

The fourth scenario symptom is eye movements and eye responses related to the concussion symptom of eye or ocular pain. With a concussion, trauma to the head can cause accommodation spasms (e.g., muscles of the eye contracting for extended periods of time), leading to redness, burning, itchiness, pain, etc. When executing the fourth scenario symptom, the system 100 generates simulated eye movements and simulated eye responses to allow a medical trainee to assess eye movement and eye responses related to eye or ocular pain. A medical trainee uses verbal communication and/or mere observation of the simulated eyes 102 as the external input. A verbal communication can be the medical trainee asking the computer device 104 if pain exists. This can be detected by the microphone and analyzed using voice recognition techniques to determine if the medical trainee asked the correct question. In some embodiments, the application software displays a textual response (via the display 106) and/or generates an audible response (via a speaker) confirming or denying that there is pain. Under the normal state, the textual and/or audible response is a confirmation that there is no pain. Under the fourth scenario, the textual and/or audible response is a confirmation that there is pain. In addition, or in the alternative, the sclera 102d, 102i of the simulated eye 102 can appear to be red and/or pink (mimicking irritation to the eye). Thus, under a normal state the first sclera 102d and the second sclera 102i is white. Under the fourth scenario, the computer device 104 causes the first sclera 102d and/or the second sclera 102i to appear red and/or pink.

The fifth scenario symptom is eye movements and eye responses related to the concussion symptom of abnormal eye movements. Abnormal eye movement can be defined as weakened or delayed movements, as characterized by slowed or delayed tracking of and/or focusing on objects (e.g., non-smooth pursuit eye movement), a scan or shift of visual focus from one object to another (e.g., saccades) gaze instability the inability to maintain focus while the head is moving), etc. When executing the fifth scenario symptom, the system 100 generates simulated eye movements and simulated eye responses to allow a medical trainee to assess eye movement and eye responses related to abnormal eye movements.

Assessing Non-Smooth Pursuit Eye Movement

A medical trainee uses a stylus 110 movement with a voice command to ask the computer device 104 to "track the stylus". Under a normal state, each of the first pupil 102b and the second pupil 102g follows the stylus tip 112 so that maintains aim on the stylus tip 112 (i.e., each of the first pupil 102b and the second pupil 102g maintain aim on a same point in space, which is the stylus tip 112). Under the fifth scenario, the first pupil 102b and/or the second pupil 102g exhibits a slowed or delayed tracking of the stylus tip 112 as the stylus 110 is moved. As a non-limiting example, the stylus tip 112 may be positioned in front of the display 106 at $L_{ONG3}$, $L_{AT2}$ and moved to $L_{ONG2}$, $L_{AT2}$. Under the fifth scenario, the first pupil 102b and the second pupil 102g tracks the stylus tip 112 from $L_{ONG2}$, $L_{AT2}$ to $L_{ONG2}$, $L_{AT2}$ but with a time delay.

Assessing Saccades

A medical trainee can position two styluses 110 in front of the display 106 and ask the computer device 104 to focus on the tip of one of the styluses 110. For example, a medical trainee holds a first stylus 110 and a second stylus 110 in front of the display 106, with the first tip 112 and the second tip 112 at different points in space. For instance, the first stylus tip 112 may be located at $L_{ONG3}$, $L_{AT2}$ and the second stylus tip 112 may be located at $L_{ONG2}$, $L_{AT2}$. The medical trainee asks the computer to focus on the first tip 112. Under the normal state, each of the first pupil 102b and the second pupil 102g maintains focus on the first tip 112 (e.g., each of the first pupil 102b and the second pupil 102g is continuously aimed at the first tip 112). Under the fifth scenario, the first pupil 102b and/or the second pupil 102g deviates focus from the first tip 112. This can include shifting focus to and from the first tip 112. This can further include shifting focus between the first tip 112 and the second tip 112. Focus on the stylus tip 112 is defined as the pupil 102b, 102g aiming at a point in space where the stylus tip 112 is located.

Assessing Gaze Instability

Figure 4:
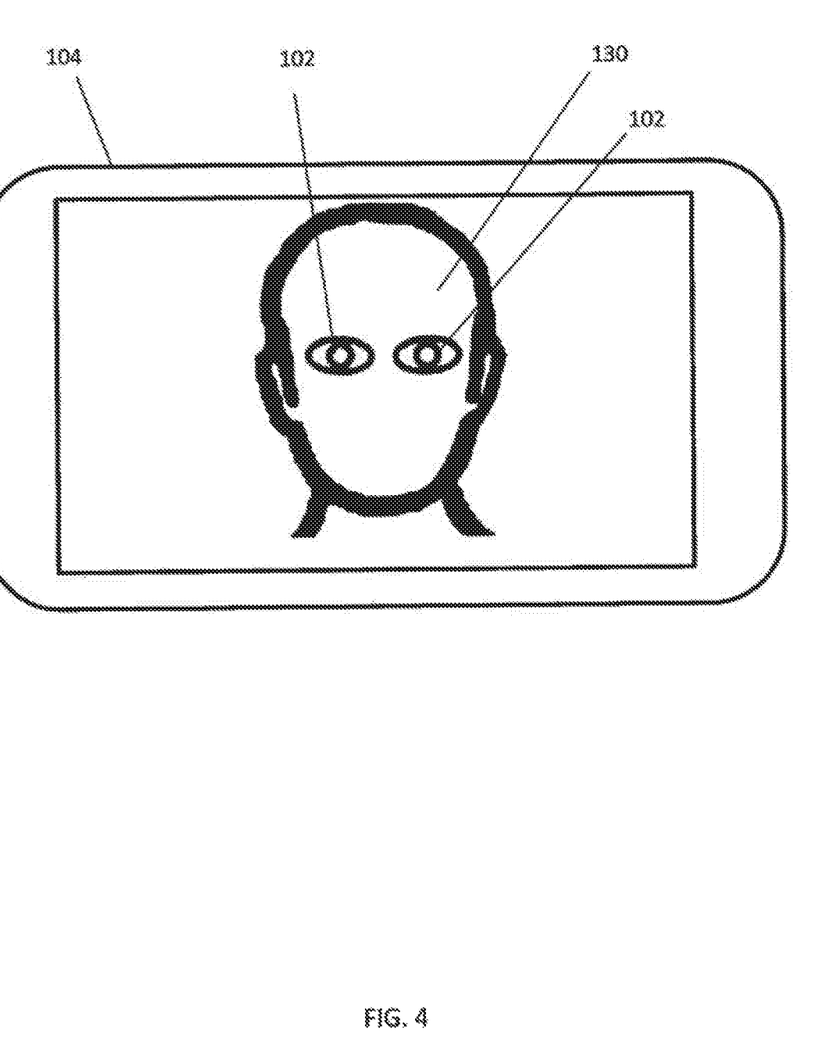
FIG. 4 shows an embodiment of the eye simulator system with a human head as part of the simulated display.

A medical trainee issues a voice command to ask the computer device 104 to "move its head" as the medical trainee executes a stylus 110 movement. Under a normal state, each of the first pupil ion and the second pupil 102g follows the stylus tip 112 so that maintains aim on the stylus tip 112 even when the "head is moving". Under the fifth scenario, the first pupil 102b and/or the second pupil 102g deviates focus from the stylus tip 112. This can include shifting focus to and from the stylus tip 112. In some embodiments, the application software is programmed to display anatomical features in addition to the simulated eyes 102. This can include displaying the head 130. (See FIG. 4). The head can be animated. Thus, when executing the fifth scenario and the head 130 is moving, the image of the head can be caused to appear to be moving left to right, up to down, etc.

The sixth scenario symptom is eye movements and eye responses related to the concussion symptom of visual motion sensitivity. Visual motion sensitivity can be defined by a sensation of being disoriented, uncomfortable, and/or having vertigo triggered by busy or disorienting environments. When executing the sixth scenario symptom, the system 100 generates simulated eye movements and simulated eye responses to allow a medical trainee to assess eye movement and eye responses related to visual motion sensitivity. A medical trainee motions at least one stylus 110 in front of the display 106 and issues a verbal command to the computer device 104 asking it if it feels disoriented, uncomfortable, dizzy, etc. Under a normal state, a textual and/or audible response is generated confirming that there is no disorientation, discomfort, and/or dizziness as medical trainee motions the at least one stylus 110. Under the sixth scenario, a textual and/or audible response is generated confirming that there is disorientation, discomfort, and/or dizziness as medical trainee motions the at least one stylus 110.

The seventh scenario symptom is eye movements and eye responses related to the concussion symptom of vertical heterophoria. Vertical heterophoria occurs when the eyes are misaligned vertically (e.g., one eye is higher than the other). The brain may try to compensate for this misalignment and generate strain or fatigue in the eye muscles. When executing the seventh scenario symptom, the system 100 generates simulated eye movements and simulated eye responses to allow a medical trainee to assess eye movement and eye responses related to vertical heterophoria. A medical trainee uses verbal communication and/or mere observation of the simulated eyes 102 as the external input. With observation as the external input, a medical trainee observes if the first pupil 102b and the second pupil are located on the same latitudinal axis. Under the normal state, each of the first pupil 102b and the second pupil 102g is located on the same latitudinal axis. Under the seventh scenario, the first pupil 102b and the second pupil 102g are not located on the same latitudinal axis. With verbal communication as the external input, a medical trainee asks the computer device 104 if there is pain or discomfort. Under a normal state, a textual and/or audible response is generated confirming that there is no pain or discomfort. Under the seventh scenario, a textual and/or audible response is generated confirming that there is pain and/or discomfort.

In some embodiments, the system 100 generates concussion tutorials. These can be textual information (via the display 106) or audio output (via a speaker) regarding the symptoms of a scenario being executed, which can include information about how a concussion causes the eye movements and eye responses associated with the symptoms of a scenario being executed. The concussion tutorials can be generated before, during, and/or after the scenario symptom is being executed by the computer device 104.

Figure 5:
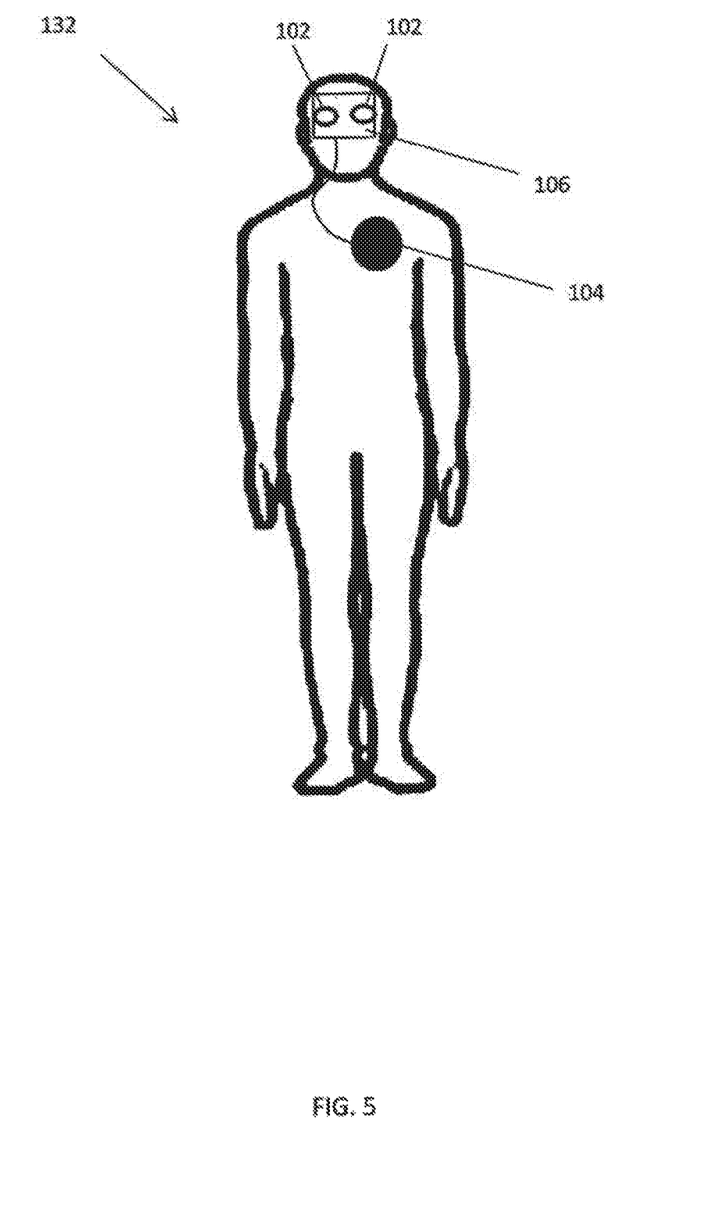
FIG. 5 shows an embodiment of the eye simulator system being used with a simulator manikin.

Referring to FIG. 5, in some embodiments, the computer device 104 is part of a manikin simulator 132. The manikin simulator 132 is a medical simulator device configured to resemble at least a portion of a human anatomy. For example, the computer device 104 can be incorporated into the manikin simulator 132, wherein the display 106 is configured to be part of an eye simulator portion of the manikin simulator 132.

Figure 6:
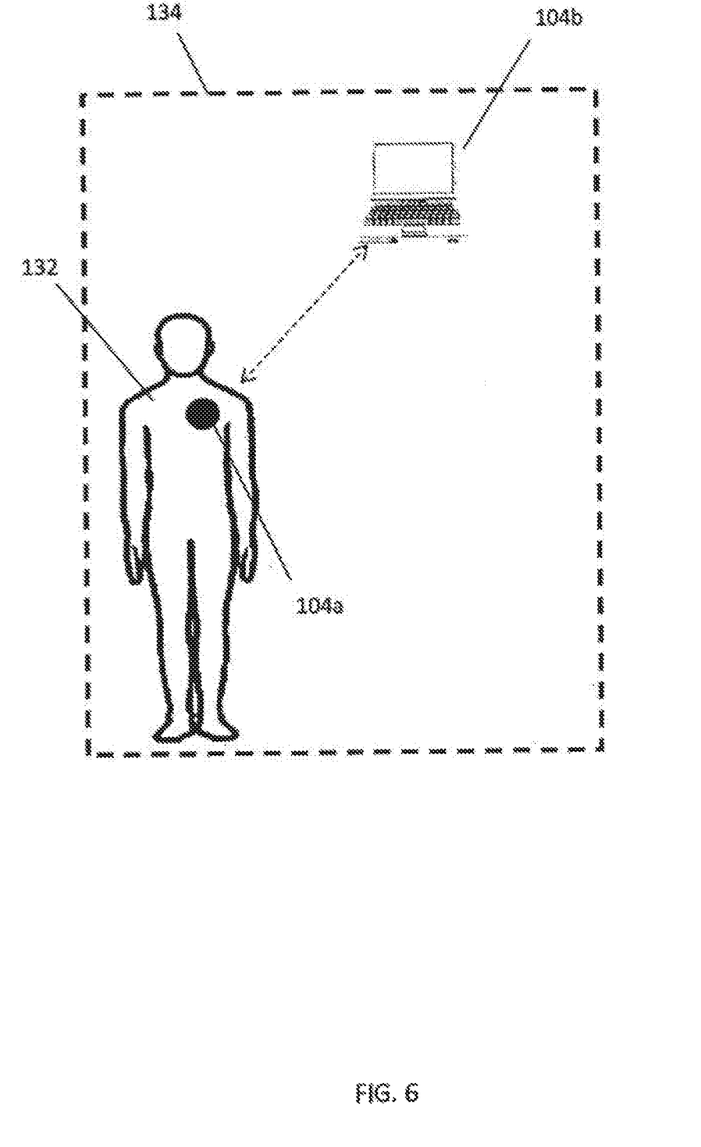
FIG. 6 shows an exemplary schematic of an embodiment of the eye simulator system with a plurality of computer devices.

Referring to FIG. 6, in some embodiments, the system 100 includes more than one computer device 104. For example, the system 100 can be part of a communications network 134 having a first computer device 104a and a second computer device 104b. The first computer device 104a can be the computer device 104 associated with the display 106, as described above. The second computer device 104b is connected to the first computer device 104a via the communications network 134. The communications network 134 can be a hardwired network or a wireless network (e.g., via transceivers). Any of the computer devices 104a, 104b of the communications network 134 are configured to receive and transmit data, manipulate data, analyze data, and send instructions to and from each other. Control of the system 100 can be via the first computer device 104a and/or the second computer device 104b. It is contemplated for a medical trainer to control aspects of the system 100 via the second computer device 104b, which can include operating parameters, selection of scenarios, etc. It is contemplated for a medical trainee to control aspects of the system 100 via the first computer device 104a, which may be limited to providing external inputs to the first computer device 104a.

It should be understood that modifications to the embodiments disclosed herein can be made to meet a particular set of design criteria. For instance, the number of or configuration of computer devices 104, communicate on networks 134, simulated eyes 102, sensors 108, manikin simulators 134, and/or other components or parameters may be used to meet a particular objective.

Additional understanding of the disclosed system and methods of use can be obtained from the materials attached as an appendix of this specification.

It will be apparent to those skilled in the art that numerous modifications and variations of the described examples and embodiments are possible in light of the above teachings of the disclosure. The disclosed examples and embodiments are presented for purposes of illustration only. Other alternative embodiments may include some or all of the features of the various embodiments disclosed herein. For instance, it is contemplated that a particular feature described, either individually or as part of an embodiment, can be combined with other individually described features, or parts of other embodiments. The elements and acts of the various embodiments described herein can therefore be combined to provide further embodiments.

Therefore, it is the intent to cover all such modifications and alternative embodiments as may come within the true scope of this invention, which is to be given the full breadth thereof. Additionally, the disclosure of a range of values is a disclosure of every numerical value within that range, including the end points. Thus, while certain exemplary embodiments of apparatuses and methods of making and using the same have been discussed and illustrated herein, it is to be distinctly understood that the invention is not limited thereto but may be otherwise variously embodied and practiced within the scope of the following claims.

What is claimed is:

1. A simulator for evaluating symptoms of a concussion, comprising:
   a computer device in operative association with a display and a stylus;
   wherein:
      the computer device is configured to generate a pair of simulated eyes via the display, the pair of simulated eyes comprising:
         a first eye comprising a first pupil; and
         a second eye comprising a second pupil;
      the display comprises a front face, a plurality of latitudinal axes, and a plurality of longitudinal axes, the first pupil being located at a first intersecting point of a latitudinal axis and a longitudinal axis and the second pupil being located at a second intersecting point of a latitudinal axis and a longitudinal axis;
      the display is configured to generate textual and/or audible responses to verbal questions or verbal commands;
      the stylus comprises a shaft and a tip, the tip including a marker;
      the computer device comprises a sensor configured to detect proximity and motion of the marker; and
      the computer device is configured to generate eye movements in accordance with at least one concussion scenario symptom and to generate eye responses to an external input, the external input comprising voice commands and movements of the stylus.

2. The simulator recited in claim 1, wherein the stylus further comprises a light source.

3. The simulator recited in claim 2, wherein the external input further comprises light from the light source.

4. The simulator recited in claim 1, wherein the at least one concussion scenario symptom comprises a plurality of concussion scenario symptoms.

5. The simulator recited in claim 4, wherein the plurality of concussion scenario symptoms comprises:
   a first scenario symptom comprising eye movements and eye responses associated with diplopia;
   a second scenario symptom comprising eye movements and eye responses associated with sensitivity to light and/or photophobia;
   a third scenario symptom comprising eye movements and eye responses associated with vision loss;
   a fourth scenario symptom comprising eye movements and eye responses associated with eye or ocular pain;
   a fifth scenario symptom comprising eye movements and eye responses associated with abnormal eye movements;
   a sixth scenario symptom comprising eye movements and eye responses associated with visual motion sensitivity; and
   a seventh scenario symptom comprising eye movements and eye responses associated with vertical heterophoria.

6. The simulator recited in claim 5, further comprising generating the pair of simulated eyes in a normal state, wherein:
   the first pupil and the second pupil are located on a same latitudinal axis; and
   the first pupil and the second pupil are separated by a constant distance $D_{eye}$.

7. The simulator recited in claim 6, wherein the first scenario symptom comprises $D_{eye}$ increasing or decreasing and/or the first pupil and/or the second pupil not being located on the same latitudinal axis as the stylus tip is moved from position $D_2$ to position $D_1$, wherein $D_2$ and $D_1$ are distances from the front face of the display, $D_2$ being a greater distance than $D_1$.

8. The simulator recited in claim 6, wherein:
   the stylus further comprises a light source;
   the first eye comprises a first eyelid;
   the second eye comprises a second eyelid; and
   the second scenario symptom comprises at least one of:
      the first eyelid and/or the second eyelid blinks, squints, or closes as the light source with an intensity and/or an angle of incidence within first predetermined ranges is shown at or near the first pupil and/or second pupil; and
      the first pupil and/or the second pupil dilates as the light source with an intensity and/or an angle of incidence within second predetermined ranges is shown at or near the first pupil and/or second pupil.

9. The simulator recited in claim 6, wherein;
the stylus further comprises a light source;
the first eye comprises a first eyelid;
the second eye comprises a second eyelid; and
the third scenario symptom comprises at least one of:
  the first pupil and/or the second pupil does not track the stylus tip as the stylus tip is moved;
  the first eyelid and/or the second eyelid does not blink, squint, or dose as the stylus tip is rapidly moved from position $D_2$ to position $D_1$, wherein $D_2$ and $D_1$ are distances from the from face of the display, $D_2$ being a greater distance than $D_1$; and
  the first pupil and/or the second pupil does not dilate as the light source with an intensity and/or an angle of incidence within third predetermined ranges is shone at or near the first pupil and the second pupil.

10. The simulator recited in claim 9, wherein:
the first pupil and/or the second pupil does not track the stylus tip as the stylus tip is moved within a blind spot;
the first eyelid and/or the second eyelid does not blink, squint, or close as the stylus tip is rapidly moved from position $D_2$ to position $D_1$, wherein $D_2$ and $D_1$ are within the blind spot;
the first pupil and/or the second pupil does not dilate as the light source with an intensity and/or an angle of incidence within fourth predetermined ranges is shone at or near the first pupil and the second pupil, the light source being within the blind spot; and
the blind spot being defined as a predetermined volume of space in front of the front face.

11. The simulator recited in claim 6, wherein:
the first eye comprises a first sclera;
the second eye comprises a second sclera; and
the fourth scenario symptom comprises at least one of:
  textual and/or audible responses to verbal questions about pain, the textual and/or audible response being a confirmation that there is pain; and
  the first sclera and/or the second sclera having a red or pink color.

12. The simulator recited in claim 6, wherein;
the fifth scenario symptom comprises at least one of;
  the first pupil and/or the second pupil exhibiting a slowed or delayed tracking of the stylus tip as the stylus tip is moved; and
  the first pupil and/or the second pupil deviating focus from the stylus tip, focus on the stylus tip being defined as the first pupil and/or the second pupil aiming at a point in space where the stylus tip is located.

13. The simulator recited in claim 6, wherein:
the sixth scenario symptom comprises motioning the stylus and textual and/or audible responses to verbal questions about disorientation, discomfort, and/or dizziness, the textual and/or audible response being a confirmation that there is disorientation, discomfort, and/or dizziness.

14. The simulator recited in claim 6, wherein:
the seventh scenario symptom comprises:
  first pupil and the second pupil not being located on the same latitudinal axis; and
  textual and/or audible responses to verbal questions about pain and/or discomfort, the textual and/or audible response being a confirmation that there is pain and/or discomfort.

15. The simulator recited in claim 1, wherein a concussion tutorial is generated for the at least one concussion scenario symptom.

* * * * *